United States Patent
Mori et al.

(10) Patent No.: US 8,852,941 B2
(45) Date of Patent: Oct. 7, 2014

(54) METHOD FOR PRODUCING INDUCED PLURIPOTENT STEM CELLS

(75) Inventors: Masaki Mori, Osaka (JP); Hideshi Ishii, Osaka (JP); Norikatsu Miyoshi, Osaka (JP); Yuichiro Doki, Osaka (JP); Masahiro Tanemura, Osaka (JP); Kenichi Nagai, Osaka (JP); Hiromitsu Hoshino, Osaka (JP); Yoshiaki Omura, Osaka (JP); Naotsugu Haraguchi, Osaka (JP); Susumu Miyazaki, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/579,314

(22) PCT Filed: Feb. 18, 2011

(86) PCT No.: PCT/JP2011/053457
§ 371 (c)(1),
(2), (4) Date: Nov. 15, 2012

(87) PCT Pub. No.: WO2011/102444
PCT Pub. Date: Aug. 25, 2011

(65) Prior Publication Data
US 2013/0065243 A1    Mar. 14, 2013

(30) Foreign Application Priority Data

Feb. 18, 2010  (JP) ................................ 2010-034008

(51) Int. Cl.
C12N 5/07       (2010.01)
C12N 15/00      (2006.01)
G01N 33/50      (2006.01)
C12N 5/074      (2010.01)

(52) U.S. Cl.
CPC .......... *C12N 5/0696* (2013.01); *C12N 2501/65* (2013.01); *C12N 2506/1384* (2013.01); *G01N 33/5008* (2013.01); *C12N 2506/1307* (2013.01)
USPC ........................................ 435/377; 435/455

(58) Field of Classification Search
USPC ................................. 435/377, 455
See application file for complete search history.

(56) References Cited

U.S. PATENT DOCUMENTS

2009/0068742 A1   3/2009  Yamanaka
2009/0246875 A1   10/2009 Yamanaka et al.
2010/0075421 A1   3/2010  Yamanaka et al.

FOREIGN PATENT DOCUMENTS

| JP | 2011-087475 | 5/2011 |
|----|-------------|--------|
| WO | 2006025802  | 3/2006 |
| WO | 2007069666  | 6/2007 |
| WO | 2009075119  | 6/2009 |
| WO | 2009091659  | 7/2009 |
| WO | 2011049099  | 4/2011 |
| WO | 2011105551  | 9/2011 |

OTHER PUBLICATIONS

Thomson et al. PNAS (Aug. 1995) 92:7844-7848.*
NIH (Stem Cells: Scientific Progress and Future Research Directions, Department of Health and Human Services, Chapter 1, pp. 1-4, Jun. 2001).*
Jaenisch et al., Cell (2008) 132: 567-582.*
Griffiths-Jones et al., "miRBase: tools for microRNA genomics," Nucleic Acid Res, 2008, 36:D154-D158.
Judson et al., "Embryonic stem cell-specific microRNAs promote induced pluripotency," Nature Biotechnology, 2009, 27(5):459-461.
Koyanagi et al., "Screening and function analysis of microRNAs which involve in induction of pluripotent stem cells from murine and human somatic cells," BMB2008, Nov. 20, 2008, p. 295 (translation provided).
Koyanagi et al., "Screening and functional analysis of microRNAs which involve in induction of pluripotent stem cells from murine somatic cells," BMB2007, Nov. 25, 2007, p. 504 (translation provided).
Lin et al., "Mir-302 reprograms human skin cancer cells into a pluripotent ES-cell-like state," RNA, 2008, 14:2115-2124.
Miyoshi et al., "Defined factors induce reprogramming of gastrointestinal cancer cells," PNAS, 2010, 107(1):40-45.
Okita et al., "Generation of Mouse Induced Pluripotent Stem Cells Without Viral Vectors," Science, 2008, 322:949-953.
Takahashi and Yamanaka, "Induction of Pluripotent Stem Cells form Mouse Embryonic and Adult Fibroblast Cultures by Defined Factors," Cell, 2006, 126:663-676.
Miyoshi et al., Reprogramming of Mouse and Human Cells to Pluripotency Using Mature MicroRNAs, Cell Stem Cell, 2011 8: 633-638; with Supplemental Information (20 pages total).

* cited by examiner

*Primary Examiner* — Jon E Angell
(74) *Attorney, Agent, or Firm* — Casimir Jones S.C.

(57) ABSTRACT

A major object of the present invention is to provide a method for producing induced pluripotent stem cells with low tumorigenesis potential and high induction efficiency.

The invention provides a method for producing induced pluripotent stem cells comprising the step of introducing one or more nucleic acids that facilitate expression of at least one gene selected from the group consisting of NANOG, SOX2, OCT3/4, KLF4, LIN28, and c-MYC into somatic cells.

8 Claims, 6 Drawing Sheets

SEQUENCE LISTING

```
<160> NUMBER OF SEQ ID NOS: 26

<210> SEQ ID NO 1
<211> LENGTH: 23
<212> TYPE: RNA
<213> ORGANISM: Mus musculus

<400> SEQUENCE: 1
caaagugcuu acagugcagg uag                                           23
```

-continued

```
<210> SEQ ID NO 2
<211> LENGTH: 22
<212> TYPE: RNA
<213> ORGANISM: Mus musculus

<400> SEQUENCE: 2
uagcuuauca gacugauguu ga                                              22

<210> SEQ ID NO 3
<211> LENGTH: 22
<212> TYPE: RNA
<213> ORGANISM: Mus musculus

<400> SEQUENCE: 3
uagguuaucc guguugccuu cg                                              22

<210> SEQ ID NO 4
<211> LENGTH: 23
<212> TYPE: RNA
<213> ORGANISM: Mus musculus

<400> SEQUENCE: 4
uaauacugcc ggguaaugau gga                                             23

<210> SEQ ID NO 5
<211> LENGTH: 22
<212> TYPE: RNA
<213> ORGANISM: Mus musculus

<400> SEQUENCE: 5
aaagugcuuc ccuuuugugu gu                                              22

<210> SEQ ID NO 6
<211> LENGTH: 22
<212> TYPE: RNA
<213> ORGANISM: Mus musculus

<400> SEQUENCE: 6
aagugcuucc auguuucagu gg                                              22

<210> SEQ ID NO 7
<211> LENGTH: 23
<212> TYPE: RNA
<213> ORGANISM: Mus musculus

<400> SEQUENCE: 7
uaagugcuuc cauguuuuag uag                                             23

<210> SEQ ID NO 8
<211> LENGTH: 22
<212> TYPE: RNA
<213> ORGANISM: Mus musculus

<400> SEQUENCE: 8
aagugcuucc auguuucagu gg                                              22

<210> SEQ ID NO 9
<211> LENGTH: 23
<212> TYPE: RNA
<213> ORGANISM: Mus musculus

<400> SEQUENCE: 9
uaagugcuuc cauguuugag ugu                                             23
```

```
<210> SEQ ID NO 10
<211> LENGTH: 22
<212> TYPE: RNA
<213> ORGANISM: Mus musculus

<400> SEQUENCE: 10
aauugcacuu uagcaauggu ga                                              22

<210> SEQ ID NO 11
<211> LENGTH: 21
<212> TYPE: RNA
<213> ORGANISM: Mus musculus

<400> SEQUENCE: 11
aauaauacau gguugaucuu u                                               21

<210> SEQ ID NO 12
<211> LENGTH: 22
<212> TYPE: RNA
<213> ORGANISM: Mus musculus

<400> SEQUENCE: 12
agaucgaccg uguuauauuc gc                                              22

<210> SEQ ID NO 13
<211> LENGTH: 22
<212> TYPE: RNA
<213> ORGANISM: Mus musculus

<400> SEQUENCE: 13
gccugcuggg guggaaccug gu                                              22

<210> SEQ ID NO 14
<211> LENGTH: 23
<212> TYPE: RNA
<213> ORGANISM: Homo sapiens

<400> SEQUENCE: 14
uaauacugcc ggguaaugau gga                                             23

<210> SEQ ID NO 15
<211> LENGTH: 23
<212> TYPE: RNA
<213> ORGANISM: Homo sapiens

<400> SEQUENCE: 15
uaagugcuuc cauguuuugg uga                                             23

<210> SEQ ID NO 16
<211> LENGTH: 23
<212> TYPE: RNA
<213> ORGANISM: Homo sapiens

<400> SEQUENCE: 16
uaagugcuuc cauguuuag uag                                              23

<210> SEQ ID NO 17
<211> LENGTH: 23
<212> TYPE: RNA
<213> ORGANISM: Homo sapiens

<400> SEQUENCE: 17
uaagugcuuc cauguuucag ugg                                             23
```

```
<210> SEQ ID NO 18
<211> LENGTH: 23
<212> TYPE: RNA
<213> ORGANISM: Homo sapiens

<400> SEQUENCE: 18
uaagugcuuc cauguuugag ugu                                              23

<210> SEQ ID NO 19
<211> LENGTH: 21
<212> TYPE: RNA
<213> ORGANISM: Homo sapiens

<400> SEQUENCE: 19
aauaauacau gguugaucuu u                                                21

<210> SEQ ID NO 20
<211> LENGTH: 22
<212> TYPE: RNA
<213> ORGANISM: Homo sapiens

<400> SEQUENCE: 20
agaucgaccg uguuauauuc gc                                               22

<210> SEQ ID NO 21
<211> LENGTH: 21
<212> TYPE: DNA
<213> ORGANISM: Artificial Sequence
<220> FEATURE:
<223> OTHER INFORMATION: PCR primer: Nanog-S

<400> SEQUENCE: 21
ttcttgctta caagggtctg c                                                21

<210> SEQ ID NO 22
<211> LENGTH: 18
<212> TYPE: DNA
<213> ORGANISM: Artificial Sequence
<220> FEATURE:
<223> OTHER INFORMATION: PCR primer: Nanog-AS

<400> SEQUENCE: 22
cagggctgcc ttgaagag                                                    18

<210> SEQ ID NO 23
<211> LENGTH: 20
<212> TYPE: DNA
<213> ORGANISM: Artificial Sequence
<220> FEATURE:
<223> OTHER INFORMATION: PCR primer: Oct3/4-S

<400> SEQUENCE: 23
cacgagtgga aagcaactca                                                  20

<210> SEQ ID NO 24
<211> LENGTH: 20
<212> TYPE: DNA
<213> ORGANISM: Artificial Sequence
<220> FEATURE:
<223> OTHER INFORMATION: PCR primer: Oct3/4-AS

<400> SEQUENCE: 24
gctttcatgt cctgggactc                                                  20
```

```
<210> SEQ ID NO 25
<211> LENGTH: 19
<212> TYPE: DNA
<213> ORGANISM: Artificial Sequence
<220> FEATURE:
<223> OTHER INFORMATION: PCR primer: Gadph-S

<400> SEQUENCE: 25
tgtccgtcgt ggatctgac                                                19

<210> SEQ ID NO 26
<211> LENGTH: 20
<212> TYPE: DNA
<213> ORGANISM: Artificial Sequence
<220> FEATURE:
<223> OTHER INFORMATION: PCR primer: Gadph-AS

<400> SEQUENCE: 26
cctgcttcac caccttcttg                                               20
```

METHOD FOR PRODUCING INDUCED PLURIPOTENT STEM CELLS

This application is a national stage of International Application No. PCT/JP2011/053457, filed Feb. 18, 2011, which claims priority to Japanese Patent Application No. 2010-034008, filed Feb. 18, 2010, both of which are incorporated by reference herein in their entireties for any purpose.

TECHNICAL FIELD

The present invention mainly relates to a method for producing induced pluripotent stem cells using nucleic acids, in particular, microRNAs.

BACKGROUND ART

Regenerative medicine is highly expected to provide medical means for healing irreparable damage of body parts due to accidental injuries or diseases. In particular, development of a method for healing damaged tissues by transplantation of regenerated cells derived from the injured patient is expected to solve the problem of immune rejection, and thereby greatly reduce the burdens of patients and medical institutions. So far, regeneration of some body parts, such as skin or cornea, has been studied as a medical treatment based on such regenerative medicine.

However, currently, regenerative medicine can be applied only to the limited tissues. One of the hindrances to the advancement of regenerative medicine is the unavailability of cells capable of pluripotent differentiation and self-replication; such cells can be differentiated into various cells, tissues and organs. After the fetus period, humans develop cells capable of pluripotent differentiation and self-replication that can be differentiated into particular cells and tissues; however, humans do not have pluripotent stem cells capable of pluripotent differentiation and self-replication that can be differentiated into various cells. A method for establishing strains of embryonic stem cells (ES cell), which are pluripotent stem cells, has been developed for mice used as model organisms; however, production of human ES cells is greatly hindered by ethical restrictions, as it requires disruption of an undeveloped early embryo to obtain target cells. Therefore, individualized ES cell production for each patient has so far been virtually impossible.

Given this situation, production of induced pluripotent stem cells by way of reprogramming of somatic cells (iPS cells) is attracting attention as a technique that enables production of pluripotent stem cells from readily available somatic cells. This technique is characterized by introduction of nuclear reprogramming factors OCT3/4, SOX2, c-MYC, AND KLF4 into somatic cells (Patent Literature 1). In contrast to hitherto-known technologies, the use of an iPS cell production technique is expected to enable production of pluripotent stem cells for various patients, thus enabling regeneration of organs and nerves that have been considered irreparable.

However, some drawbacks have been reported regarding the induced pluripotent stem cells, including tumorigenesis of transplanted cells and inefficiency in the production. Such drawbacks are considerable issues in the application of the induced stem cells in clinical use. Assumed causes of tumorigenesis include introduction of proto-oncogene c-Myc and induction of cancer-inducing mutation due to introduction of genes into the genome. Regarding low efficiency in production of induced pluripotent stem cells, more trial and error is necessary to find effective induction other than the methods using genome insertion. To solve these problems, research has been conducted for (1) a method for attempting induction after removing cancer genes from the introducing cells, (2) a method using proteins or a method of introducing plasmid, and (3) a method using various virus vectors. However, so far, these methods are all insufficient for practical use in the medical industry due to insufficient introduction efficiency, etc.

Under such circumstances of the prior art, there has been a demand for the development of a technology for producing satisfactory induced pluripotent stem cells for practical use in the medical industry.

CITATION LIST

Patent Literature (PTL)

PTL 1: International Publication 2007/069666

Non-Patent Literature (NPL)

NPL 1: SCIENCE, 2008, 322; 949-953.
NPL 2: NUCLEIC ACID RESEARCH, 2008, 36; D154-D158.
NPL 3: CELL, 2006, 126; 663-676.
NPL 4: PROCEEDINGS OF THE NATIONAL ACADEMY OF SCIENCES OF THE UNITED STATES OF AMERICA, 2010, 107: 40-45.

SUMMARY OF INVENTION

Technical Problem

A major object of the present invention is to provide a method for producing induced pluripotent stem cells with low possibility of tumorigenesis and high induction efficiency. The present invention also provides an inducer of the induced pluripotent stem cells and an induced pluripotent stem cell-producing kit to be used for the method for producing induced pluripotent stem cells, as well as a method for screening an inducing factor that enables production of induced pluripotent stem cells.

Solution to Problem

The present inventors conducted intensive studies to solve the aforementioned problems and, to their surprise, found a method for producing induced pluripotent stem cells not involving gene integration. This method introduces, as a nuclear reprogramming factor, one or more microRNAs that facilitate expression of at least one gene selected from the group consisting of NANOG, SOX2, OCT3/4, KLF4, LIN28, and c-MYC. Even more surprisingly, this production method, which does not require gene integration, was also found to produce induced pluripotent stem cells with low tumorigenesis and high induction efficiency. The present inventors conducted further research based on these findings, and completed the present invention.

Specifically, the present invention encompasses the following aspects.

[Item 1]
A method for producing induced pluripotent stem cells comprising the step of introducing a nuclear reprogramming factor into somatic cells,
wherein
the nuclear reprogramming factor is one or more nucleic acids that facilitate expression of at least one gene selected from the group consisting of NANOG, SOX2, OCT3/4, KLF4, LIN28, and c-MYC.

[Item 2]
The method according to Item 1, wherein the nucleic acids are microRNAs.

[Item 3]
The method according to Item 2, wherein the microRNAs include at least one microRNA selected from the group consisting of microRNAs that suppress differentiation, microRNAs that promote induction of undifferentiation, microRNAs that control cell-cell adhesion, and microRNAs that suppress apoptosis.

[Item 4]
The method according to Item 2 or 3, wherein the microRNAs are miR-200, miR-302, and miR-369.

[Item 5]
Induced pluripotent stem cells produced by the method according to any one of Items 1 to 4.

[Item 6]
An inducer of induced pluripotent stem cells containing one or more nucleic acids that facilitate expression of at least one gene selected from the group consisting of NANOG, SOX2, OCT3/4, KLF4, LIN28, and c-MYC.

[Item 7]
A kit for producing induced pluripotent stem cells containing one or more nucleic acids that facilitate expression of at least one gene selected from the group consisting of NANOG, SOX2, OCT3/4, KLF4, LIN28, and c-MYC.

[Item 8]
A method for screening nucleic acids capable of producing induced pluripotent stem cells, comprising the steps of:
(1) introducing one or more test nucleic acids into somatic cells;
(2) culturing the somatic cells to which the test nucleic acids are introduced in Step (1); and
(3) selecting the test nucleic acids as nucleic acids capable of producing induced pluripotent stem cells when induced pluripotent stem cells are induced in the somatic cells cultured in Step (2).

[Item 9]
The method according to Item 8, wherein induction of induced pluripotent stem cells is detected based on facilitation of expression of at least one gene selected from the group consisting of NANOG, SOX2, OCT3/4, KLF4, LIN28, and c-MYC.

[Item 10]
The method according to Item 8 or 9, wherein the nucleic acids are microRNAs.

Advantageous Effect of Invention

In contrast to the hitherto-known technologies of producing induced pluripotent stem cells that require introduction of genes including proto-oncogene into somatic cells, the method of the present invention enables production of induced pluripotent stem cells with low tumorigenesis without requiring gene integration, by adopting a method of introducing, as a nuclear reprogramming factor, one or more nucleic acids that facilitate expression of at least one gene selected from NANOG, SOX2, OCT3/4, KLF4, LIN28, and c-MYC into cells. Moreover, in addition to such an advantage, the method of the present invention accomplishes high induction efficiency in the production of induced pluripotent stem cells. The induced pluripotent stem cells produced by the method of the present invention can be a useful tool for regenerative medicine, by being adopted as materials of artificial tissues and organs including artificial skin, muscles, and nerves.

DESCRIPTION OF EMBODIMENTS

Figure 1:
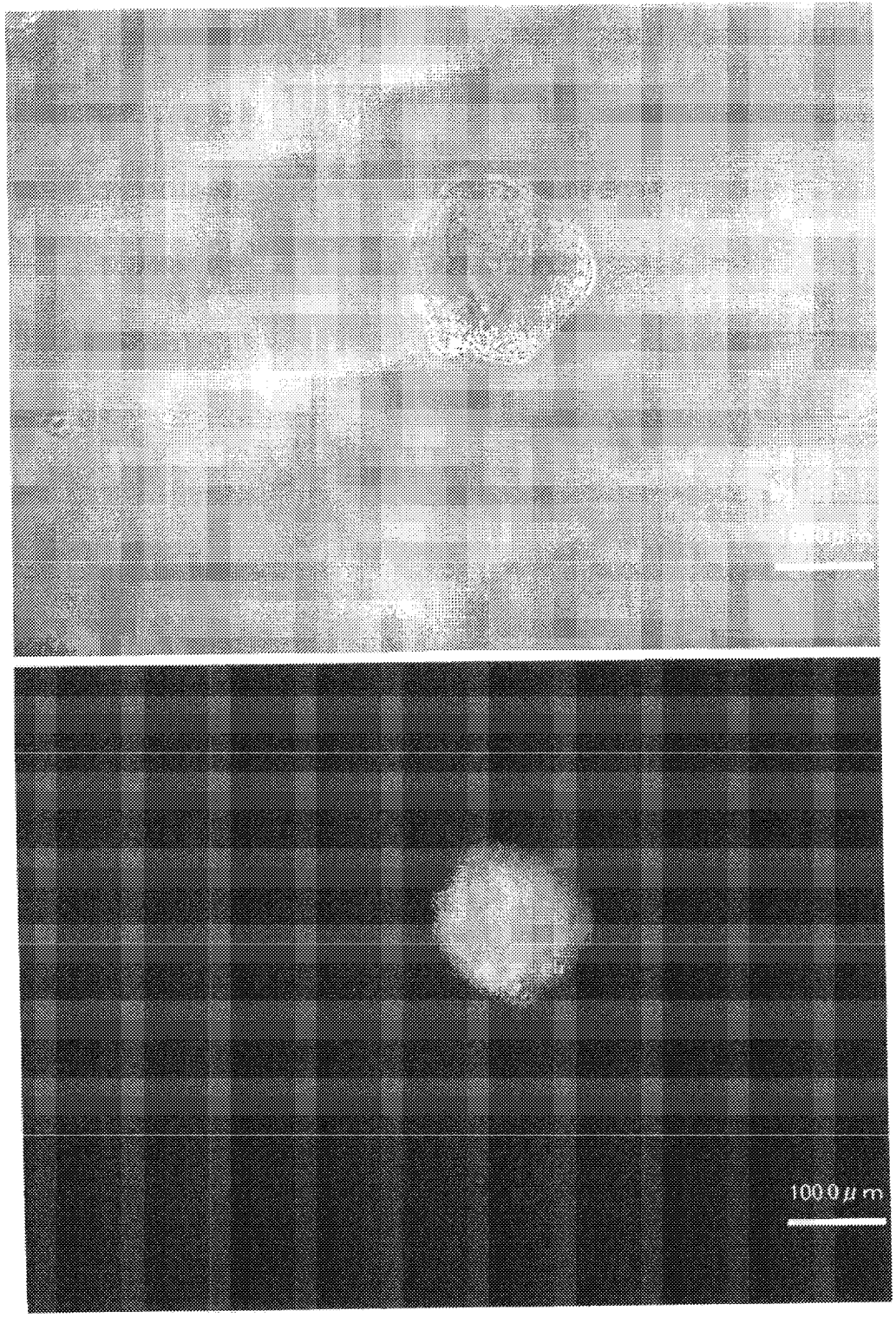
FIG. 1 shows induced pluripotent stem cells produced using mouse adipose-derived stem cells according to the method of the present invention (Example 1). The upper panel shows a phase-contrast image, whereas the lower panel shows a fluorescent image of NANOG-GFP. The scale bar indicates 100 μm.

A primary object of the present invention is to provide a method for producing induced pluripotent stem cells, an inducer of induced pluripotent stem cells, a kit for producing induced pluripotent stem cells, and a method for screening nucleic acids capable of producing induced pluripotent stem cells. Hereunder, the production method, inducer, kit, and screening method are described in this order.

In the present invention, induced pluripotent stem cells refer to somatic cell-derived cells that possess pluripotency and self-proliferation capability by introducing a pluripotent inducing factor (nuclear reprogramming factor) that reprograms somatic cells.

1. Method for Producing Induced Pluripotent Stem Cells

The method for producing induced pluripotent stem cells of the present invention comprises the step of introducing a nuclear reprogramming factor into somatic cells, wherein the nuclear reprogramming factor is one or more nucleic acids that facilitate expression of at least one gene selected from the group consisting of NANOG, SOX2, OCT3/4, KLF4, LIN28, and c-MYC. The production method of the present invention is described in detail below.

In the present invention, induced pluripotent stem cells are produced from somatic cells. The somatic cells are preferably normal cells among normal cells and tumor (cancer) cells. There is no particular limitation on the types of the cells, and any somatic cells may be used. Examples of somatic cells used in the present invention include fibroblasts, epithelial cells, muscle cells (e.g., skeletal muscle cells and visceral muscle cells), hepatic cells, bone cells, vascular endothelial cells, brain neurons, glia (oligodendroglia and astroglia), primary, secondary, tertiary, and subsequent spheres derived from various cells including brain neurons, glia, and cancer cells, peripheral blood- or bone marrow-derived mononuclear cells, granular leukocytes, and lymphocytes, osteoblasts, osteoclasts, gastric epithelial cells, liver epithelial cells, small and large intestinal tract epithelial cells, pancreatic cells (endocrine cells such as alpha cells and beta cells, and exocrine cells), and adipose-derived stem cells (ADSCs). Of these somatic cells, fibroblasts and adipose-derived stem cells are preferable, and adipose-derived stem cells are more preferable from the viewpoint that expression of at least one gene selected from the group consisting of NANOG, SOX2, OCT3/4, KLF4, LIN28, and c-MYC is efficiently facilitated by introduction of one or more nucleic acids. Fibroblasts and adipose-derived stem cells are also preferable from the viewpoint of ready availability of somatic cells.

The above-mentioned somatic cells are suitably selected from somatic cells from mammals such as humans, mice, rats, hamsters, rabbits, cats, dogs, sheep, pigs, bovines, goats, monkeys, and the like according to the intended purpose of induced pluripotent stem cells. When the produced induced pluripotent stem cells are used as tools in regenerative medicine in humans or as tools for development of diagnostic drugs, it is preferable to use somatic cells derived from humans. Further, when somatic cells derived from humans are used, somatic cells derived from any of fetuses, infants, children, and adults may be used.

Regarding the somatic cells, somatic cells removed from a mammal may be used, or commercially available somatic cells may be used. Further, in either the case of using somatic cells removed from a mammal or using commercially available somatic cells, the obtained somatic cells can be grown by a known technique and used. When induced pluripotent stem cells are produced for the purpose of transplant into human patients, somatic cells derived from any of a patient and another person may be used. Producing induced pluripotent stem cells using somatic cells derived from a patient is suitable for producing induced pluripotent stem cells that do not exhibit immune rejection with respect to the patient. Producing induced pluripotent stem cells using somatic cells derived from another person is suitable for producing induced pluripotent stem cells having none of the patient's genetic diseases.

The one or more nucleic acids of the present invention that are a nuclear reprogramming factor may include DNA, RNA, etc., and are not particularly limited as long as they facilitate expression of at least one gene selected from the group consisting of NANOG, SOX2, OCT3/4, KLF4, LIN28, and c-MYC, which are endogenous to the above-mentioned somatic cells. As specific examples of the nucleic acids, low molecular weight RNAs of about 18 to about 120 bases, preferably about 18 to about 80 bases, and more preferably about 18 to about 26 bases, or DNAs capable of expressing the low molecular weight RNAs can be mentioned. The nucleic acids are particularly preferably the low molecular weight RNAs. Specific examples of the low molecular weight RNAs include, but are not limited to, non-coding RNAs such as microRNAs (miRNAs) and siRNAs. The low molecular weight RNAs are preferably microRNAs. In addition, the DNAs capable of expressing the low molecular weight RNAs are preferably known expression vector DNAs into which sequences corresponding to the low molecular weight RNAs are incorporated.

MicroRNAs, which are single-stranded RNAs mainly possessed by animal cells, are believed to have a function to suppress expression of a particular target gene or a group of target genes. With respect to microRNAs, it is believed that after direct transcriptional product pri-miRNAs (primary miRNAs) undergo processing to form pre-miRNAs, pre-miRNAs further undergo processing to form mature microRNAs. Pre-miRNAs comprise a base length of about 60 to about 80 bases. Mature microRNAs comprise a base length of about 18 to about 26 bases. When the nucleic acids of the present invention are microRNAs, any of precursors pri-miRNAs and pre-miRNAs, as well as mature microRNAs may be used. The microRNAs are preferably pre-miRNAs or mature microRNAs, and more preferably mature microRNAs.

siRNAs are double-stranded RNAs of about 21 to about 23 base pairs. siRNAs are believed to cause a phenomenon referred to as RNA interference, in which expression of a gene that a target mRNA encodes is suppressed by destroying the mRNA.

In the present invention, induced pluripotent stem cells are produced by introducing, into somatic cells, one or more nucleic acids that facilitate expression of at least one gene selected from the group consisting of NANOG, SOX2, OCT3/4, KLF4, LIN28, and c-MYC. The nucleic acids of the present invention are not particularly limited, as long as they facilitate expression of at least one gene selected from the group consisting of NANOG, SOX2, OCT3/4, KLF4, LIN28, and c-MYC. The nucleic acids are preferably those that facilitate expression of NANOG and/or OCT3/4, and more preferably those that facilitate expression of NANOG. It is desirable that the genes are endogenous to somatic cells.

With respect to the aforementioned genes, the following are known. NANOG encodes a homeodomain-containing transcription factor, is specifically expressed in germ-line cells in the development of mammals, and is believed to play an important role in maintaining self-replication capability and pluripotency of the germ-line cells. SOX2 (SRY (sex determining region Y)-box 2) encodes an HMG box-containing transcription factor. OCT3/4 (also known as POU5F1) encodes a POU-type homeodomain-containing transcription factor and is known to be specifically expressed in germ-line cells in the development of mammals. The SOX2 transcription factor and the OCT3/4 transcription factor can form a dimer and are believed to cooperatively contribute to suppression of induction of differentiation of germ-line cells. KLF4 (Kruppel-Like Factor 4) encodes a transcription factor with homology to a transcription factor encoded by the Drosophila Kruppel gene, and the KLF4 transcription factor is known to have a function of controlling cell differentiation by cell cycle-related factor control. LIN28 is homologous to the lin-28 gene of the nematode C. elegans, and is believed to encode an RNA-binding protein that plays an important role in maintaining pluripotency of stem cells. c-MYC encodes a transcription factor containing a bHLH motif and a leucine zipper motif, and the c-MYC transcription factor is believed to be involved in expression of a wide range of genes. In addition, c-MYC is also known as a proto-oncogene, which is a gene that can become an oncogene due to mutations. As a technique for producing induced pluripotent stem cells, a method in which OCT3/4, SOX2, c-MYC, and KLF4 are introduced into somatic cells in mice and a method in which NANOG, OCT3/4, SOX2, and LIN28 are introduced into somatic cells in humans is reported (Patent Literature 1 and Non-patent Literature 1). Specifically, these genes are believed to play an important role in obtaining self-replication capability and pluripotency of cells. In particular, NANOG and OCT3/4, which are specifically expressed in germ-line cells, are believed to play an extremely important role in achieving self-replication capability and pluripotency of cells.

The nucleic acids of the present invention may be used singly, or in a combination of two or more as long as the above-mentioned conditions are met. The nucleic acids of the present invention may be, for example, a combination of different types of nucleic acids, such as a combination of RNA and DNA; a combination of different types of RNA, such as a combination of a microRNA and a siRNA; or the like. It is preferable to use a combination of two or more nucleic acids from the viewpoint of efficiently facilitating expression of at least one gene selected from the group consisting of NANOG, SOX2, OCT3/4, KLF4, LIN28, and c-MYC, preferably NANOG and/or OCT3/4, and more preferably NANOG. In addition, from the viewpoint of achieving high efficiency of induction of pluripotency, it is preferable to use a combination of 10 or fewer nucleic acids, and more preferable to use a combination of 7 or fewer nucleic acids in order not to impair the effect of individual nucleic acids included in the combination.

When the nucleic acids of the present invention are microRNAs or DNAs capable of expressing microRNAs, although they are not particularly limited, only the microRNAs or the DNAs capable of expressing microRNAs may be substantially used as a nuclear reprogramming factor that is introduced into somatic cells for producing induced pluripotent stem cells. Specifically, the production method of the present invention may be a method that comprises the step of introducing the microRNAs or the DNAs capable of expressing microRNAs into somatic cells and in which a nuclear reprogramming factor other than the microRNAs or the DNAs capable of expressing microRNAs (for example, compounds that singly or in combination can produce induced pluripotent stem cells such as nucleic acids other than microRNAs or DNAs capable of expressing microRNAs, and proteins) that singly or in combination can produce induced pluripotent stem cells) is not substantially introduced into somatic cells. Here, "not substantially introduced into somatic cells" refers to not introducing, into somatic cells, an amount in a range that can attain the effect of somatic cell reprogramming.

When the nucleic acids of the present invention are microRNAs, microRNAs that facilitate expression of at least one gene selected from the group consisting of NANOG, SOX2, OCT3/4, KLF4, LIN28, and c-MYC, preferably NANOG and/or OCT3/4, and more preferably NANOG can be suitably selected by those skilled in the art by a known technique or the like. The same is true of the case where the nucleic acids of the present invention are DNAs capable of expressing microRNAs.

As the microRNAs, it is preferable to use microRNAs that are expressed in at least one selected from undifferentiated cells, such as ES cells, and cancer cells that are commonly known to have acquired pluripotency and self-replication capability; and it is more preferable to use microRNAs whose expression amount varies (is facilitated or decreased, and more preferably facilitated) in the cells compared to that in common differentiated cells. The types of undifferentiated cells are not particularly limited, and are preferably human or mouse ES cells. The types of cancer cells are not particularly limited, and examples thereof include colorectal cancer cells, colon cancer cells, esophageal cancer cells, stomach cancer cells, pancreatic cancer cells, hepatic cancer cells, and bile duct cancer cells. From the aforementioned viewpoint, as an example of microRNAs that facilitate expression of at least one gene selected from the group consisting of NANOG, SOX2, OCT3/4, KLF4, LIN28, and c-MYC, preferably NANOG and/or OCT3/4, and more preferably NANOG, at least one microRNA selected from the group consisting of miR-17, miR-21, miR-154, miR-200, miR-294, miR-302, miR-367, miR-369, miR-370, miR-371, miR-372, miR-373, miR-374, miR-376 (also known as miR-368) and miR-424 can be mentioned; and at least one microRNA selected from the group consisting of miR-17, miR-154, miR-200, miR-294, miR-302, miR-367, miR-369, and miR-370 can be preferably mentioned.

Further, from the viewpoint that pluripotent stem cells have pluripotency and self-proliferation capability, microRNAs that facilitate expression of at least one gene selected from the group consisting of NANOG, SOX2, OCT3/4, KLF4, LIN28, and c-MYC, preferably NANOG and/or OCT3/4, and more preferably NANOG are those including at least one microRNA selected from the following Group A, Group B, Group C, and Group D; preferably at least one microRNA selected from the following Group A, Group B, and Group C, or from the following Group A, Group B, and Group D; and more preferably a combination of the following Group A, Group B, and Group C, or a combination of the following Group A, Group B, and group D. However, the microRNAs are not limited thereto.

Group A: microRNAs that suppress differentiation;
Group B: microRNAs that promote induction of undifferentiation;
Group C: microRNAs that control cell-cell adhesion; and
Group D: microRNAs that suppress apoptosis.

The introduction of microRNAs of the above Group A into somatic cells is believed to further activate pluripotency of the somatic cells into which the microRNAs are introduced, by suppression of promotion of differentiation, and the like. The introduction of microRNAs of the above Group B into somatic cells is believed to further activate pluripotency of the somatic cells into which the microRNAs are introduced, by promotion of an undifferentiated state. The introduction of microRNAs of the above Group C into somatic cells is believed to further activate self-proliferation capability of the somatic cells into which the microRNAs are introduced, by release of contact inhibition, and the like. The introduction of microRNAs of the above Group D into somatic cells is believed to suppress cell death due to apoptosis of the somatic cells into which the microRNAs are introduced, relatively increase cell viability, and further activate self-proliferation capability of the somatic cells. Specifically, it is believed that facilitation of expression of at least one gene selected from the group consisting of NANOG, SOX2, OCT3/4, KLF4, LIN28, and c-MYC, preferably NANOG and/or OCT3/4, and more preferably NANOG is achieved by the function of microRNAs of the above Group A, Group B, Group C, and Group D, i.e., the function of further activating pluripotency and/or self-proliferation capability of somatic cells.

Specific microRNAs of the above Group A, Group B, Group C, and Group D can be suitably selected by those skilled in the art. Specific examples of each group are mentioned below; however, the microRNAs of each group are not limited to the specific microRNAs described below.

Group A: miR-294, miR-302, miR-367, miR-369, miR-370, miR-371, miR-372, miR-373, miR-374, miR-376 (also known as miR-368), miR-424, and the like;
Group B: miR-17, miR-369, and the like;
Group C: miR-200, and the like; and
Group D: miR-17, miR-21, and the like.

As a specific combination of microRNAs, the following can be mentioned; however, the combination is not limited thereto. A combination of miR-302, miR-367, miR-369, miR-370, miR-17, miR-21, and miR-154 can be mentioned as microRNAs including Group A, Group B, and Group D. A combination of miR-302, miR-369, and miR-200; a combination of miR-294, miR-302, miR-369, and miR-200; or the like can be mentioned as microRNAs of a combination of Group A, Group B, and Group C.

The above-described microRNAs are commonly present in mammals including humans. Although microRNAs derived from an optionally chosen mammal may be used, it is desirable to suitably select microRNAs according to the origin of somatic cells into which the microRNAs are introduced. For example, when somatic cells derived from humans are used, it is desirable that the microRNAs to be introduced into the somatic cells are derived from humans.

The base sequences of pre-miRNAs and mature microRNAs of the aforementioned microRNAs, which are published in the miRBase database maintained and operated by the Faculty of Life Sciences at the University of Manchester, United Kingdom, are known (URL: http://www.mirbase.org/). miRBase is described in Non-patent Literature 2, and the like. Accession numbers of the microRNAs are exemplified below.

Pre-miRNA miR-17: hsa-miR-17 (human, miRBase accession number MI0000071), mmu-miR-17 (mouse, miRBase accession number MI0000687);

miR-21: hsa-miR-21 (human, miRBase accession number MI0000077), mmu-miR-21 (mouse, miRBase accession number MI0000569);

miR-154: hsa-miR-154 (human, miRBase accession number MI0000480), mmu-miR-154 (mouse, miRBase accession number MI0000176);

miR-200: hsa-miR-200a (human, miRBase accession number MI0000737), mmu-miR-200a (mouse, miRBase accession number MI0000554), hsa-miR-200b (human, miRBase accession number MI0000342), mmu-miR-200b (mouse, miRBase accession number MI0000243), hsa-miR-200c (human, miRBase accession number MI0000650), mmu-miR-200c (mouse, miRBase accession number MI0000694);

miR-294: mmu-miR-294 (mouse, miRBase accession number MI0000392);

miR-302: hsa-miR-302a (human, miRBase accession number MI0000738), mmu-miR-302a (mouse, miRBase accession number MI0000402), hsa-miR-302b (human, miRBase accession number MI0000772), mmu-miR-302b (mouse, miRBase accession number MI0003716), hsa-miR-302c (human, miRBase accession number MI0000773), mmu-miR-302c (mouse, miRBase accession number MI0003717), hsa-miR-302d (human, miRBase accession number MI0000774), mmu-miR-302d (mouse, miRBase accession number MI0003718), hsa-miR-302e (human, miRBase accession number MI0006417), hsa-miR-302f (human, miRBase accession number MI0006418);

miR-367: hsa-miR-367 (human, miRBase accession number MI0000775), mmu-miR-367 (mouse, miRBase accession number MI0003531);

miR-369: hsa-miR-369 (human, miRBase accession number MI0000777), mmu-miR-369 (mouse, miRBase accession number MI0003535);

miR-370: hsa-miR-370 (human, miRBase accession number MI0000778), mmu-miR-370 (mouse, miRBase accession number MI0001165);

miR-371: hsa-miR-371 (human, miRBase accession number MI0000779);

miR-372: hsa-miR-372 (human, miRBase accession number MI0000780);

miR-373: hsa-miR-373 (human, miRBase accession number MI0000781);

miR-374: hsa-miR-374a (human, miRBase accession number MI0000782), mmu-374b (human, miRBase accession number MI0005566), mmu-miR-374, (mouse, miRBase accession number MI0004125);

miR-376 (also known as miR-368): hsa-miR-376c (human, miRBase accession number MI0000776), mmu-miR-376c (mouse, miRBase accession number MI0003533); and miR-424: hsa-miR-424 (human, miRBase accession number MI0001446).

Mature miRNA miR-17: hsa-miR-17 (human, miRBase accession number MIMAT0000070), mmu-miR-17 (mouse, miRBase accession number MIMAT0000649);

miR-21: hsa-miR-21 (human, miRBase accession number MIMAT0000076), mmu-miR-21 (mouse, miRBase accession number MIMAT0000530);

miR-154: hsa-miR-154 (human, miRBase accession number MIMAT0000452), mmu-miR-154 (mouse, miRBase accession number MIMAT0000164);

miR-200: hsa-miR-200a (human, miRBase accession number MIMAT0000682), mmu-miR-200a (mouse, miRBase accession number MIMAT0000519), hsa-miR-200b (human, miRBase accession number MIMAT0000318), mmu-miR-200b (mouse, miRBase accession number MIMAT0000233), hsa-miR-200c (human, miRBase accession number MIMAT0000617), mmu-miR-200c (mouse, miRBase accession number MIMAT0000657);

miR-294: mmu-miR-294 (mouse, miRBase accession number MIMAT0000372);

miR-302: hsa-miR-302a (human, miRBase accession number MIMAT0000684), mmu-miR-302a (mouse, miRBase accession number MIMAT0000380), hsa-miR-302b (human, miRBase accession number MIMAT0000715), mmu-miR-302b (mouse, miRBase accession number MIMAT0003374), hsa-miR-302c (human, miRBase accession number MIMAT0000717), mmu-miR-302c (mouse, miRBase accession number MIMAT0003376), hsa-miR-302d (human, miRBase accession number MIMAT0000718), mmu-miR-302d (mouse, miRBase accession number MIMAT0003377), hsa-miR-302e (human, miRBase accession number MIMAT0005931), hsa-miR-302f (human, miRBase accession number MIMAT0005932);

miR-367: hsa-miR-367 (human, miRBase accession number MIMAT0000719), mmu-miR-367 (mouse, miRBase accession number MIMAT0003181);

miR-369: hsa-miR-369-3p (human, miRBase accession number MIMAT0000721), hsa-miR-369-5p (human, miRBase accession number MIMAT0001621), mmu-miR-369-3p (mouse, miRBase accession number MIMAT0003186), mmu-miR-369-5p (mouse, miRBase accession number MIMAT0003185);

miR-370: hsa-miR-370 (human, miRBase accession number MIMAT0000722), mmu-miR-370 (mouse, miRBase accession number MIMAT0001095);

miR-371, hsa-miR-371-3p (human, miRBase accession number MIMAT0000723), hsa-miR-371-5p (human, miRBase accession number MIMAT0004687);

miR-372, hsa-miR-372 (human, miRBase accession number MIMAT0000724);

miR-373, hsa-miR-373 (human, miRBase accession number MIMAT0000726);

miR-374, hsa-miR-374a (human, miRBase accession number MIMAT0000727), mmu-374b (human, miRBase accession number MIMAT0004955), mmu-miR-374, (mouse, miRBase accession number MIMAT0003727);

miR-376 (also known as miR-368): hsa-miR-376c (human, miRBase accession number MIMAT0000720), mmu-miR-376c (mouse, miRBase accession number MIMAT0003183); and miR-424: hsa-miR-424 (human, miRBase accession number MIMAT0001341).

Regarding microRNAs having a plurality of known pre-miRNA or mature microRNA sequences (e.g., miR-200, miR-302, miR-369, miR-371, miR-374, and the like) among the above microRNAs, microRNAs of one or more sequences selected from the group consisting of the plurality of sequences may be used as long as they fulfill the function of facilitating expression of at least one gene selected from the group consisting of NANOG, SOX2, OCT3/4, KLF4, LIN28, and c-MYC, preferably NANOG and/or OCT3/4, and more preferably NANOG. For example, regarding miR-200, it is preferable to use miR-200c; however, the miR-200 is not limited thereto. Regarding miR-302, it is preferable to use a combination of miR-302a, miR-302b, miR-302c, and miR-302d; however, the miR-302 is not limited thereto. Regarding miR-369, it is preferable to use miR-369-5p alone, or a combination of miR-369-3p and miR-369-5p; however, the miR-369 is not limited thereto.

The microRNAs can be, in addition to wild-type microRNAs, mutant-type microRNAs in which one or several (e.g., 1 to 10, preferably 1 to 6, more preferably 1 to 4, still more preferably 1 to 3, particularly preferably 1 or 2) bases in the base sequence are substituted, deleted, and/or inserted, as long as the mutant-type microRNAs have a function of suppressing expression of a target gene or a group of genes that is equal to or greater than the function of the wild-type microRNAs.

The nucleic acids of the present invention can be prepared according to an ordinary method. For example, the nucleic acids can be synthesized by chemosynthesis or enzyme catalysis based on known sequence information. When the nucleic acids are DNA, a known recombinant DNA technique can be used. In particular, when the nucleic acids are microRNAs, they can be prepared by extracting the nucleic acids from optionally chosen mammalian cells. When the nucleic acids are low molecular weight RNAs, they are preferably prepared by chemosynthesis from the viewpoint of ease of control of preparation.

The introduction of the nucleic acids into somatic cells can be carried out by a known technique. Specifically, as a method for introducing the nucleic acids into somatic cells, the lipofection method, the microinjection method, the gene gun method, and the like can be mentioned. Of these, the lipofection method is preferable from the viewpoint of introduction efficiency, as well as efficiency of reversion of cells after introduction treatment. There is no particular limitation on transfection reagents used for carrying out the lipofection method, as long as the lipofection method can be conducted. Specific examples of preferred transfection reagents include the cationic transfection reagents Lipofectamine Reagent (Invitrogen) and Lipofectamine2000 Reagent (Invitrogen); however, the transfection reagents are not limited thereto.

The amount of the nucleic acids to be introduced into somatic cells can be suitably set by those skilled in the art. For example, when the aforementioned low molecular weight RNA is introduced into somatic cells by the lipofection method, lipofection can be carried out by diluting it (each low molecular weight RNA in the case where more than one low molecular weight RNA is introduced into somatic cells) in a solution containing the above-mentioned transfection reagent so that the concentration becomes about 10 to about 50 pM, preferably about 20 to about 40 pM, more preferably about 25 to about 35 pM, and particularly preferably about 30 pM.

By continuously culturing for about 7 to about 35 days, and preferably about 14 to about 35 days, the somatic cells into which the one or more nucleic acids are introduced in the above manner are reprogrammed; thereby, induced pluripotent stem cells are produced. Specific cell culture duration and various culture conditions such as atmosphere and a medium can be suitably selected by those skilled in the art in a range that is not particularly limited, as long as the somatic cells can be grown and induced pluripotent stem cells are produced. For example, the somatic cells can be cultured in a FBS (Fetal Bovine Serum)-containing D-MEM medium (Dulbecco's Modified Eagle Medium) for about 0.5 to about 2 days after introduction of the nucleic acids; or, if necessary, for about 2 to about 5 days. After that, the cells can be cultured in a known ES cell culture environment. Examples of the known ES cell culture environment include, but are not limited to, a medium in which one or more additives are added to FBS-containing D-MEM. As the additives, one or more of NEAA (Non-Essential Amino Acids), L-glutamine, 2-mercaptoethanol, LIF (Leukemia Inhibitory Factor), and the like can be selected, if necessary; however, the additives are not limited thereto. In addition, the ES cell culture environment can be one in which feeder cells are supplied, as necessary. Usable feeder cells include, for example, but are not limited to, mouse embryonic fibroblasts (MEF).

If required, cells induced into induced pluripotent stem cells can be selected from somatic cells into which the aforementioned nucleic acids are introduced. Such selection of induced pluripotent stem cells can be conducted, for example, by using the presence or absence of expression of a particular marker gene or increase or decrease in the expression amount of a particular marker gene as an index; or by using morphological changes of cells as an index.

In the case of using the presence or absence of expression of a particular marker gene or increase or decrease in the expression amount of a particular marker gene as an index, genes known to be expressed in undifferentiated cells, such as NANOG, SOX2, OCT3/4, KLF4, LIN28, and c-MYC, preferably NANOG or OCT3/4, and more preferably NANOG may be used as a marker gene. When these genes are used as a marker gene, for example, expression of the genes or the facilitation of expression amount of the genes can be used as an index for selecting induced pluripotent stem cells.

Known methods can be used as a method for detecting the presence or absence of expression of a marker gene or increase or decrease in the expression amount of a marker gene. Examples thereof include, but are not limited to, detecting the expression of mRNA of a marker gene by quantitative real-time RT-PCR or Northern analysis; detecting promoter activity of a marker gene by a construct (e.g., those inserted into the genome of cells, or those that cells retain on a plasmid) in which a reporter gene (e.g., fluorescent proteins such as green fluorescent proteins (GFP) and modified forms thereof) is linked to the promoter of the marker gene; and detecting expression of a gene product of a marker gene by immunocytochemistry. From the viewpoint of ease of handling, it is preferable to use a construct in which a fluorescent protein is linked to the promoter of a marker gene. For example, in the case of using somatic cells removed from NANOG-GFP mice as disclosed in Non-patent Literature 3, in which a NANOG promoter-GFP gene reporter construct is inserted into the genome, the facilitation of GFP expression can be used as an index for selecting induced pluripotent stem cells. When a gene product of a marker gene is a cell membrane surface molecule, induced pluripotent stem cells can be selected by sorting based on the presence or absence of expression of the cell membrane surface molecule or based on the increase or decrease in the expression amount of the cell membrane surface molecule, by a known technique using a cell sorter.

In the case of using morphological changes of cells as an index for selecting induced pluripotent stem cells, morphological changes used as an index are not particularly limited, as long as induced pluripotent stem cells can be selected. For example, embryoid bodies, which are spherical cell masses formed when ES cells having pluripotency and the like are cultured, can be used as an index. The morphological changes of cells as an index, such as embryoid bodies, can be confirmed visually, for example, by microscopic observation by a known method.

Additionally, if necessary, the selected cells can be evaluated as having properties as pluripotent stem cells. As an evaluation method, confirmation means applied to known methods of establishing ES cells can be used. Specifically, detection of a stem cell marker, evaluation of differentiation capability, and evaluation of self-replication capability can be mentioned; however, the evaluation method is not limited thereto. This evaluation method can also be used as the above-described method for selecting cells induced into induced pluripotent stem cells.

Examples of stem cell markers to be detected include, but are not limited to, alkaline phosphatase activity; SSEA1 (Stage-Specific Embryonic Antigen-1) antigen; and expression of a gene, such as NANOG, SOX2, OCT3/4, KLF4, LIN28, and c-MYC, or of the protein that the gene encodes. Specific detection methods are known; for example, detection by immunocytochemistry is suitable.

Examples of methods for evaluating differentiation capability include, but are not limited to, the following methods: adding a differentiation inducing factor to a medium in culturing the above-mentioned cells, and then detecting the achievement of differentiation into a desired cell type; and transplanting the above-mentioned cells into the body (preferably subcutaneously) of an animal from which the cells are derived, and then observing formation of teratoma. Alternatively, evaluating differentiation capability can be conducted by transplanting the above-mentioned cells into a blastocyst of an animal from which the cells are derived, and verifying birth of chimeric progeny having cells derived from the above-mentioned cells; and, more preferably, verifying birth of progeny having cells derived from the above-mentioned cells by crossing with the chimeric organism.

Evaluation of self-replication capability can be carried out, for example, by subculturing the above-described cells; self-replication capability is indicated by cell growth and a state such that the properties of the cells after the cell growth are not changed by the subculture. However, the evaluation method is not limited thereto.

In addition, the rate of tumorigenesis of the cells can be evaluated. A known technique can be used for evaluating the rate of tumorigenesis. For example, the cells can be transplanted into the body (for example, subcutaneously) of an animal from which the cells are derived to evaluate the presence or absence of tumorigenesis.

2. Inducer of Induced Pluripotent Stem Cells and Kit for Producing Induced Pluripotent Stem Cells As mentioned above, induced pluripotent stem cells can be prepared by introducing, into somatic cells as a nuclear reprogramming factor, one or more nucleic acids that facilitate expression of at least one gene selected from the group consisting of NANOG, SOX2, OCT3/4, KLF4, LIN28, and c-MYC, preferably NANOG and/or OCT3/4, and more preferably NANOG, in the method for producing induced pluripotent stem cells, which comprises the step of introducing a nuclear reprogramming factor. Therefore, the present invention further provides an inducer of induced pluripotent stem cells containing the nucleic acids, and use of the nucleic acids for the production of the inducer.

The inducer of the present invention contains the one or more nucleic acids described in "1. Method for Producing Induced Pluripotent Stem Cells" above. The details are as described in the same.

The inducer is introduced into somatic cells. The introduction of the inducer into somatic cells can be carried out by a known technique. Specifically, as a method for introducing the inducer into somatic cells, the lipofection method, the microinjection method, the gene gun method, and the like can be mentioned. Of these, the lipofection method is preferable from the viewpoint of introduction efficiency, as well as efficiency of reversion of cells after introduction treatment. There is no particular limitation on transfection reagents used when the lipofection method is carried out, as long as the lipofection method can be conducted. Specific examples of preferred transfection reagents include, but are not limited to, the cationic transfection reagents Lipofectamine Reagent (Invitrogen) and Lipofectamine2000 Reagent (Invitrogen).

The inducer is provided specifically, for example, in the form of a dry powder-like or pellet-like solid of the nucleic acids or solution of the nucleic acids. However, the form is not limited thereto. The inducer may contain other components as long as the function of facilitating expression of at least one gene selected from the group consisting of NANOG, SOX2, OCT3/4, KLF4, LIN28, and c-MYC, preferably NANOG and/or OCT3/4, and more preferably NANOG is not impaired. Further, when the inducer is a solution of the nucleic acids, the solvent is not particularly limited, as long as the function of the inducer is not impaired; for example, water, a buffer solution (e.g., Tris/EDTA-containing buffer solution), a physiological saline, and the like can be mentioned.

Further, the present invention also provides a kit for producing induced pluripotent stem cells, the kit containing one or more nucleic acids that facilitate expression of at least one gene selected from the group consisting of NANOG, SOX2, OCT3/4, KLF4, LIN28, and c-MYC, preferably NANOG and/or OCT3/4, and more preferably NANOG. The kit of the present invention contains the above-described inducer. Additionally, the kit of the present invention may contain other components in addition to the inducer, if necessary. The other components can be reagents or instruments required for producing induced pluripotent stem cells. Specific examples thereof include, but are not limited to, reagents (e.g., transfection reagents) or instruments used for introducing the nucleic acids into cells; reagents (e.g., antibodies) or instruments (e.g., slide glass, cover glass) used for selecting induced pluripotent stem cells; reagents (e.g., liquid medium) or instruments (e.g., dishes) used for cell culture; and positive control samples and negative control samples. Further, the kit of the present invention may contain a document that describes procedures for conducting the method for producing induced pluripotent stem cells of the present invention.

The kit of the present invention can be produced by containing the above components according to an ordinary method.

3. Screening Method

The present invention further provides a method for screening low molecular weight RNAs capable of producing induced pluripotent stem cells, comprising the steps of:

(1) introducing one or more test nucleic acids into somatic cells;
(2) culturing the somatic cells to which the test nucleic acids are introduced in Step (1); and
(3) selecting the test low molecular weight RNAs as nucleic acids capable of producing induced pluripotent stem cells when induced pluripotent stem cells are induced in the somatic cells cultured in Step (2).

Each step is described in detail below.

Step (1) is a step of introducing one or more test nucleic acids into somatic cells to obtain the somatic cells into which the test nucleic acids are introduced.

There is no particular limitation on the somatic cells, as long as the screening method can be achieved; the somatic cells mentioned in "1. Method for Producing Induced Pluripotent Stem Cells" above may be used.

The test nucleic acids to be screened can include DNA, RNA, etc., and are not particularly limited as long as the screening method can be achieved. The test nucleic acids are preferably those that regulate expression of at least one of genes that are endogenous to the aforementioned somatic cells. The test nucleic acids are more preferably low molecular weight RNAs of about 18 to about 120 bases, preferably about 18 to about 80 bases, and more preferably about 18 to about 26 bases, or DNAs capable of expressing the low molecular weight RNAs. The test nucleic acids are particularly preferably the low molecular weight RNAs. Specific examples of the low molecular weight RNAs include, but are not limited to, non-coding RNAs such as microRNAs (miRNAs) and siRNAs. The low molecular weight RNAs are preferably microRNAs. In addition, the DNAs capable of expressing the low molecular weight RNAs are preferably known expression vector DNAs into which sequences corresponding to the low molecular weight RNAs are incorporated.

When the test nucleic acids are microRNAs, microRNAs derived from an optionally chosen mammal may be used, and it is desirable to suitably select microRNAs according to the origin of the somatic cells into which the microRNAs are introduced. For example, when somatic cells derived from humans are used, it is desirable to use test microRNAs derived from humans.

The test microRNAs are microRNAs that are expressed in at least one selected from undifferentiated cells, such as, for example, ES cells, and cancer cells that are commonly known to have acquired pluripotency and self-replication capability. Specific examples of such microRNAs are mentioned in "1. Method for Producing Induced Pluripotent Stem Cells" above; however, the microRNAs are not limited thereto.

Further, the test microRNAs can be, in addition to wild-type microRNAs, mutant-type microRNAs in which one or several (e.g., 1 to 10, preferably 1 to 6, more preferably 1 to 4, still more preferably 1 to 3, particularly preferably 1 or 2) bases in the base sequence of wild-type microRNAs are substituted, deleted, and/or inserted.

The test nucleic acids can be obtained by the methods mentioned in "1. Method for Producing Induced Pluripotent Stem Cells" above; however, the method for obtaining the test nucleic acids is not limited thereto.

The test nucleic acids may be used singly, or in a combination of two or more, and introduced into somatic cells. From the viewpoint of efficiently carrying out screening using a plurality of test nucleic acids to be screened, it is preferable to use a combination of two or more, preferably four or more, and more preferably six or more nucleic acids. From the viewpoint of not impairing the effect of individual nucleic acids included in the combination, it is preferable to introduce a combination of 10 or fewer nucleic acids, and preferably a combination of 7 or fewer nucleic acids into somatic cells.

In the step of introducing the test nucleic acids into the somatic cells, a specific method for introducing the test nucleic acids into the somatic cells is not particularly limited, as long as the screening method can be achieved; the methods mentioned in "1. Method for Producing Induced Pluripotent Stem Cells" above can be used.

Next, Step (2) is a step of culturing the cells into which the test nucleic acids are introduced in Step (1).

The method for culturing the cells is not particularly limited, as long as the screening method can be achieved; for example, the methods mentioned in "1. Method for Producing Induced Pluripotent Stem Cells" above can be used.

Next, Step (3) is a step of selecting the test nucleic acids as nucleic acids capable of producing induced pluripotent stem cells when induced pluripotent stem cells are induced in the cells cultured in Step (2).

The induction of induced pluripotent stem cells in the cells cultured in Step (2) can be evaluated using a known method. Examples of usable known methods include, but are not limited to, the methods mentioned in "1. Method for Producing Induced Pluripotent Stem Cells" above, i.e., the method of selecting cells induced into induced pluripotent stem cells, and the method of evaluating that the cells have properties as pluripotent stem cells. The method for evaluating the induction of induced pluripotent stem cells, for example, detects facilitation of expression of at least one gene selected from the group consisting of NANOG, SOX2, OCT3/4, KLF4, LIN28, and c-MYC, preferably NANOG and/or OCT3/4, and more preferably NANOG.

In the cells cultured in Step (2), it is desirable that induced pluripotent stem cells are induced in preferably one or more cases among $1 \times 10^7$ cells into which the test nucleic acids are introduced in Step (1), more preferably one or more cases among $1 \times 10^6$ cells, and particularly preferably one or more cases among $1 \times 10^5$ cells.

When the selected nucleic acids are a combination of two or more nucleic acids, this screening method can be repeated, if necessary, by excluding one nucleic acid or two or more nucleic acids from the combination, and/or by adding one nucleic acid or two or more nucleic acids not included in the combination of two or more nucleic acids. By repeating the method, nucleic acids essential for producing induced pluripotent stem cells, and/or nucleic acids capable of producing induced pluripotent stem cells with high efficiency, can be selected.

In this manner, nucleic acids capable of producing induced pluripotent stem cells can be screened.

EXAMPLES

The present invention is more specifically explained below with reference to Examples, etc. The present invention is, however, not limited to these examples.

Examples 1 to 3

An experiment was performed to produce induced pluripotent stem cells by reprogramming mouse adipose-derived stem cells (ABSC).

Experiment Procedure

Mouse adipose-derived stem cell (ABSC) strains were established from an NANOG-GFP mouse in accordance with the method disclosed in Non-Patent Literature 4, and cultured. Each group of the cultured ABSC strains was mixed with a solution obtained by diluting 5 µl/ml of Lipofectamine 2000 and chemically synthesized micro RNAs of one of the following combinations with a serum-free medium in an amount of $2 \times 10^5$ cells/ml, thereby transfecting microRNAs into cells.

Example 1: mmu-miR-17 (SEQ ID NO: 1), mmu-miR-21 (SEQ ID NO: 2), mmu-miR-154 (SEQ ID NO: 3), mmu-miR-302a (SEQ ID NO: 5), mmu-miR-302b (SEQ ID NO: 6), mmu-miR-302c (SEQ ID NO: 7), mmu-miR-302d (SEQ ID NO: 8), mmu-miR-367 (SEQ ID NO: 10), mmu-miR-369-5p (SEQ ID NO: 12), and mmu-miR-370 (SEQ ID NO: 13);

Example 2: mmu-miR-200c (SEQ ID NO: 4), mmu-miR-294 (SEQ ID NO: 5), mmu-miR-302a (SEQ ID NO: 5), mmu-miR-302b (SEQ ID NO: 6), mmu-miR-302c (SEQ ID NO: 7), mmu-miR-302d (SEQ ID NO: 8), mmu-miR-369-3p (SEQ ID NO: 11), and mmu-miR-369-5p (SEQ ID NO: 12); and Example 3: mmu-miR-200c (SEQ ID NO: 4), mmu-miR-302a (SEQ ID NO: 6), mmu-miR-302b (SEQ ID NO: 7), mmu-miR-302c (SEQ ID NO: 8), mmu-miR-302d (SEQ ID NO: 9), mmu-miR-369-3p (SEQ ID NO: 11), and mmu-miR-369-5p (SEQ ID NO: 12).

The microRNAs were diluted so that the final concentration of each microRNA group became 30 pM upon transfection.

In each Example, the somatic cells transfected with microRNAs were cultured in a 10% FBS-containing DMEM medium for 7 days. The medium was exchanged every other day. After Day 7 of the transfection, mouse embryonic fibroblasts (treated with 10 ug/ml mitomycin for 2 hours and 30 minutes) were seeded on a 0.1% gelatin-coated plate as feeder cells, and the ES cells were cultured using a culture medium obtained by adding 15% FBS, 100 uM NEAA, 2 mM L-glutamine, 100 µM 2-mercaptoethanol, and 1000 U/ml LIF to a D-MEM. The culture medium was exchanged every day. To confirm that the thus-cultured somatic cells were reprogrammed into induced pluripotent stem cells, the expression of NANOG-GFP, which indicates generation of pluripotent stem cells, was observed using an all-in-one-type fluorescence microscopy system (product of Keyence) on Day 10 and/or Day 16 of the microRNA introduction.

Results

Figure 2:
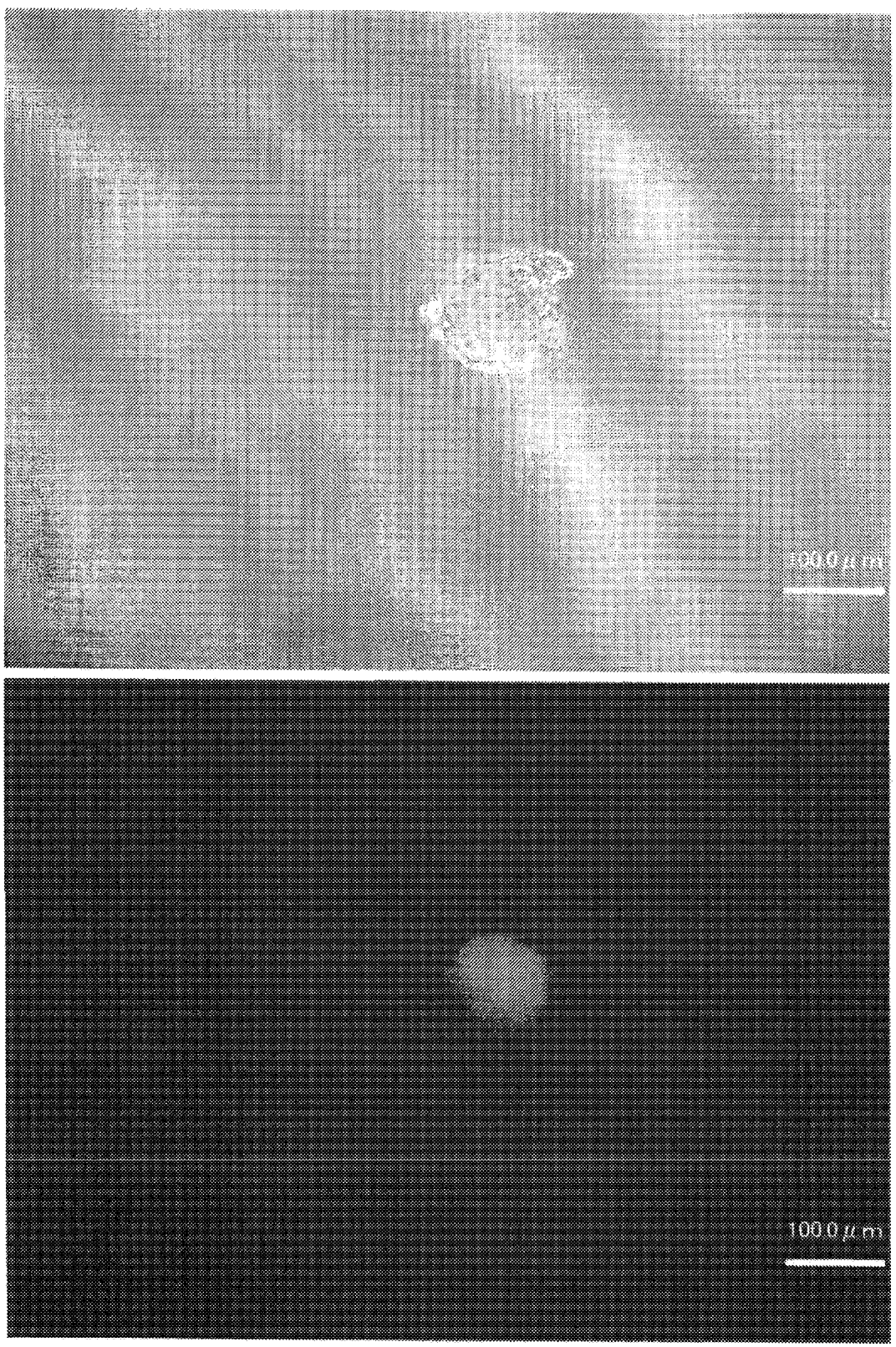
FIG. 2 shows induced pluripotent stem cells produced using mouse adipose-derived stem cells according to the method of the present invention (Example 2). The upper panel shows a phase-contrast image, whereas the lower panel shows a fluorescent image of NANOG-GFP. The scale bar indicates 100 μm.

In Examples 1 and 2, on Day 10 of the microRNA introduction, expression of the NANOG-GFP was observed in a portion of the cells. In these cells, a spherical cell mass (embryoid body), which is a distinct form of a pluripotent stem cell, was observed (FIGS. 1 and 2).

In Example 3, reprogramming into independent induced pluripotent stem cells, which was detected based on the expression of NANOG-GFP, was observed in 1 to 4 cases among $4 \times 10^5$ cells on Day 10 of the microRNA introduction, and in upto 8 cases among $4 \times 10^5$ cells on Day 16 of the microRNA introduction (ten independent experiments). These results are not inferior to the production method that produces induced pluripotent stem cells by introducing genes coding OCT3/4, KLF4, c-MYC AND SOX2 to mouse somatic cells using viral vectors (in these case, 2 to 4 cases among $4 \times 10^5$ cells on Day 10, and upto 8 cases among $4 \times 10^5$ cells on Day 16; see Non-Patent Literature 1 and 3).

Accordingly, it was confirmed that the method of the present invention enabled reprogramming of adipose-derived stem cells into induced pluripotent stem cells at a high efficiency sufficient for practical use in the medical industry.

Example 4

An immunostaining test for marker proteins was performed to verify that the induced pluripotent stem cells in Example 3 had a property similar to that of ES cells. SSEA1 antigen and OCT3/4 protein, which are known for specific expression of pluripotent cells, such as ES cells, were used as the marker proteins.

Experiment Procedure

The cells obtained in Example 3 were fixed according to an immunostaining method. The fixed sample was incubated at 4° C. for 24 hours in a phosphate buffer obtained by either diluting anti-SSEA1 antibody (MAB4301, product of Millipore) to a concentration of 10 µg/ml or diluting anti-mouse OCT3/4 antibody (MAB4305, product of Millipore) to a concentration of 20 µg/ml. After washing, the sample was further incubated at 37° C. for 30 minutes in a solution obtained by diluting a goat-derived Alexa 546 labeled anti-mouse IgG antibody (Invitrogen) serving as a secondary antibody with a phosphate buffer to a concentration of 500 ng/ml, thereby producing an antibody stained sample. The obtained sample was observed using an all-in-one-type fluorescence microscopy system (product of Keyence).

Results

Figure 3:
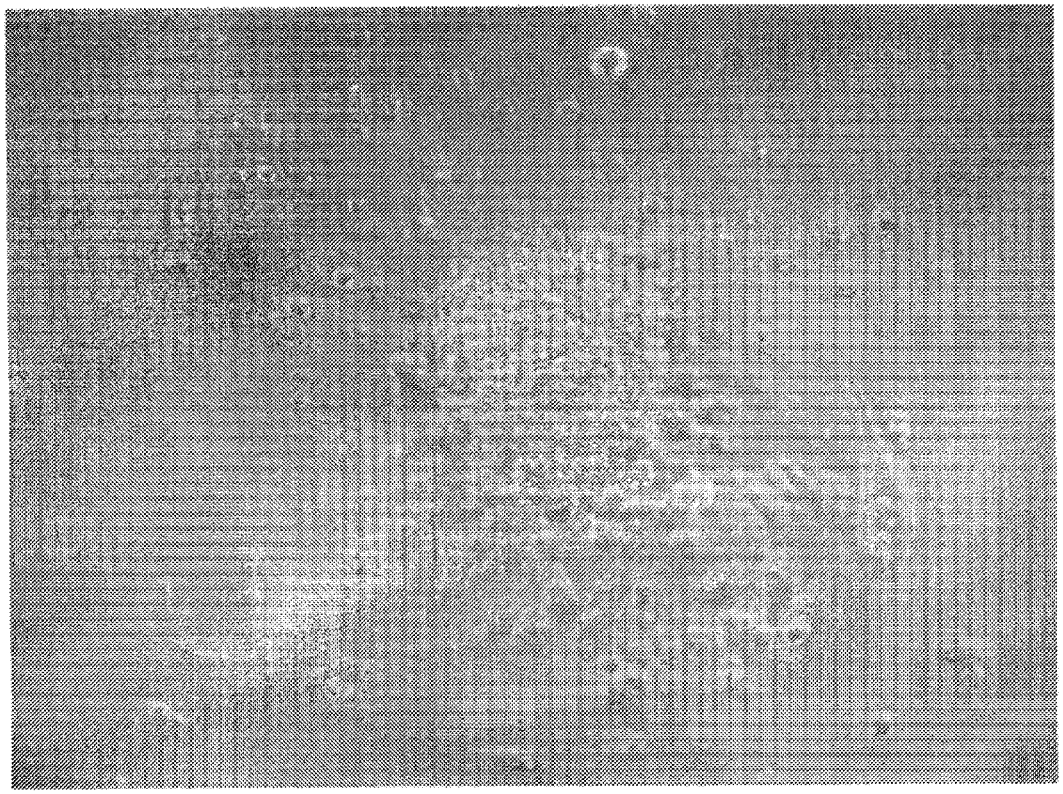
FIG. 3 shows detection of expression of SSEA1 antigen by an immunostaining method in induced pluripotent stem cells produced using mouse adipose-derived stem cells according to the method of the present invention (Example 4). The upper panel shows a phase-contrast image, whereas the lower panel shows a fluorescent image. The scale bar indicates 100 μm.
Figure 3:
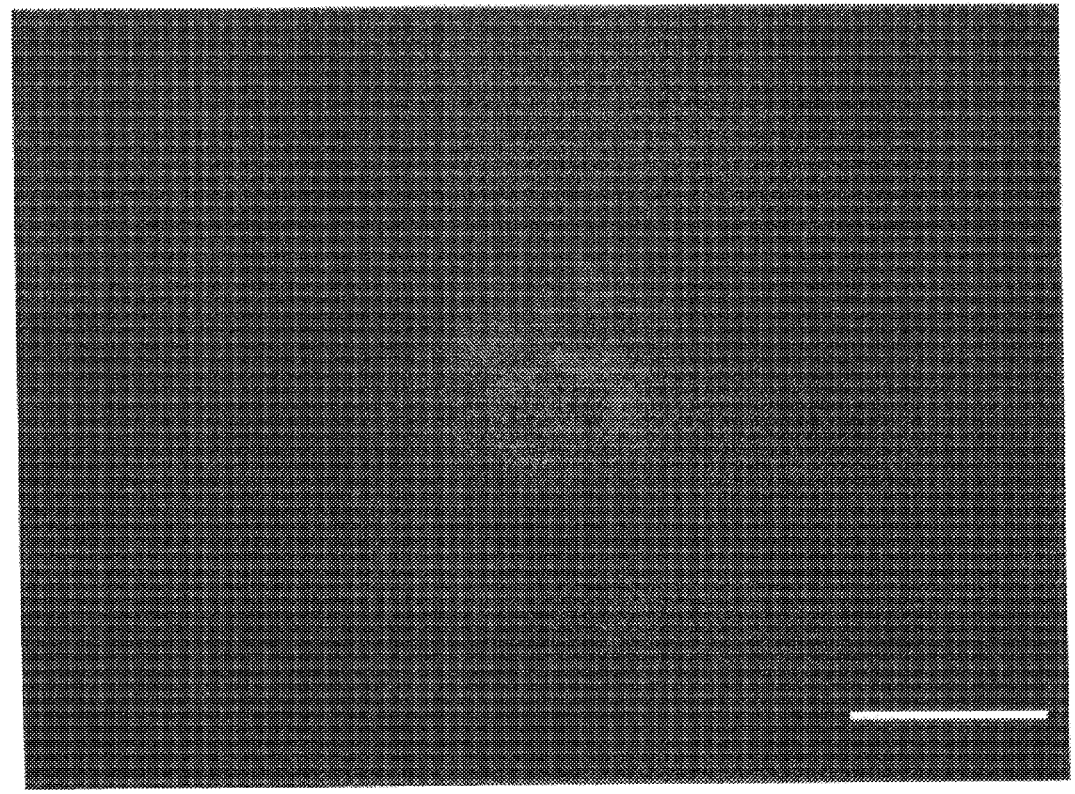
Figure 4:
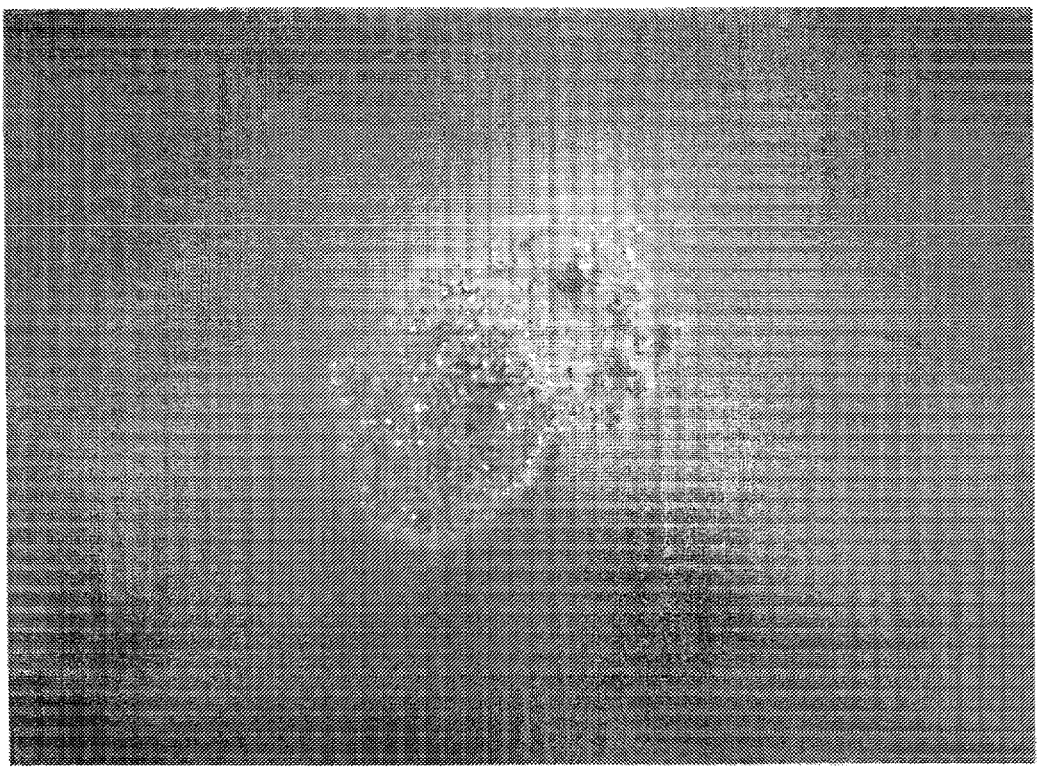
FIG. 4 shows detection of expression of the mouse OCT3/4 protein by an immunostaining method in induced pluripotent stem cells produced using mouse adipose-derived stem cells according to the method of the present invention (Example 4). The upper panel shows a phase-contrast image, whereas the lower panel shows a fluorescent image. The scale bar indicates 100 μm.
Figure 4:
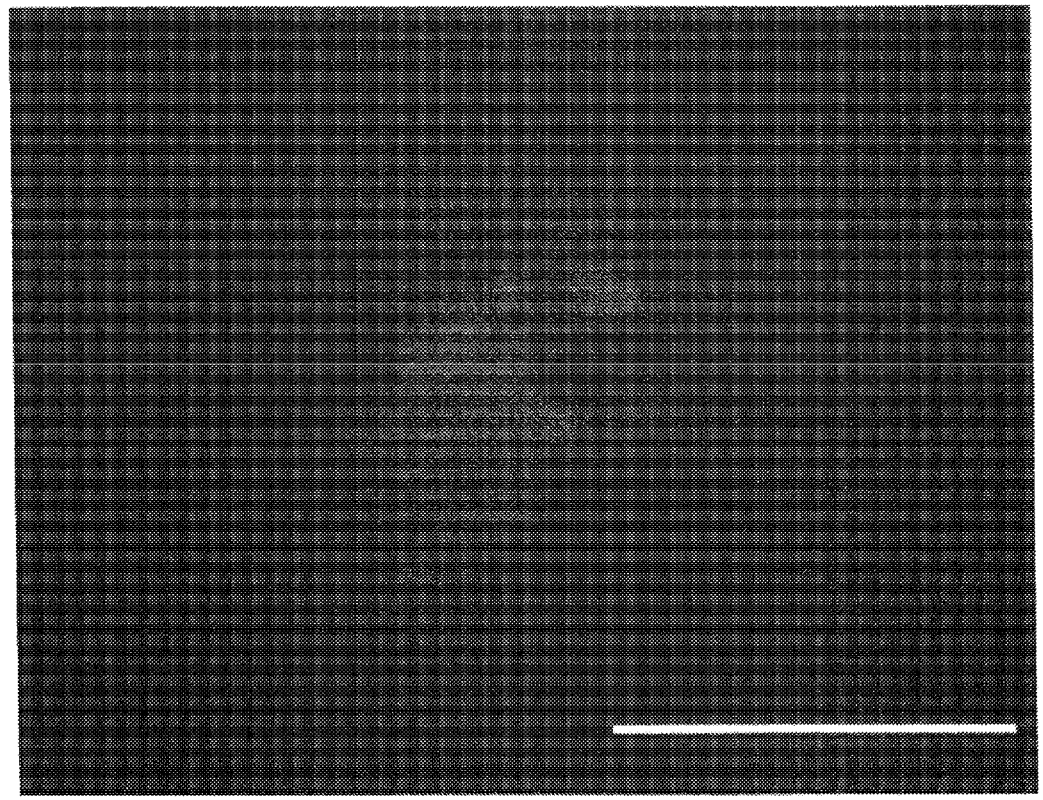

As shown in the lower image of FIG. 3, expression of mouse-SSEA1 antigen was confirmed in the colony in the central region. Further, as shown in the lower image of FIG. 4, expression of mouse-OCT3/4 protein was confirmed in the colony in the central region. It was thus confirmed that the method of the present invention successfully produced cells having a property similar to that of ES cells.

Example 5

The expression amounts of the marker genes were measured to verify that the induced pluripotent stem cells in Example 3 had a property similar to that of ES cells. Nanog gene and Oct3/4 gene, which are known for specific expression of pluripotent cells, such as ES cells, were used as the marker genes.

Experiment Procedure

An experiment was performed using the cells obtained in Example 3, a control group consisting of mouse adipose-derived stem cells cultured in a D-MEM culture medium containing 10% FBS with no microRNA introduction, and mouse ES cells (R-CMTI-1A, product of Millipore) cultured in the same manner as that of the ES cell culture in Example 3. Specifically, the somatic cells of Example 3 on Day 25 of microRNA introduction, and the mouse adipose-derived stem cells and mouse ES cells cultured for the same period as control groups were collected, and total RNA extraction was performed for each cell group using a mirVana miRNA isolation kit (AM1560, product of Ambion) according to the instructions included with the kit, thereby extracting about 2 µg total RNA from each cell group.

With 1000 ng templates of the purified RNAs thus obtained, a quantitative real-time RT-PCR was performed for mouse-NANOG and mouse-OCT3/4 using a Light Cycler TaqMan® Master kit (4535286, Roche Diagnostics), and the expression amounts were measured. The method in the instructions included with the kit was adopted for the measurement. PCR amplification was also performed for mouse-glyceraldehyde-3-phosphate dehydrogenase (GAPDH) as a positive control for confirmation of the quality of the purified RNAs and normalization of the expression amounts of the target genes.

The PCR amplification conditions were as follows. 35 cycles of a sequence of 10 seconds of heat denaturation at 95° C., and 30 seconds of annealing and extension reaction at 60° C. were performed. PCR was performed three times independently for each sample, and an average value thereof was found as the expression amount.

The following PCR primers were used:
(1) Mouse-NANOG gene:
 NANOG-S (SEQ ID NO: 21):5'-TTCTTGCTTA-CAAGGGTCTGC-3'
 NANOG-AS (SEQ ID NO: 22):5'-CAGGGCTGCCT-TGAAGAG-3'
(2) Mouse-OCT3/4 gene:
 OCT3/4-S (SEQ ID NO: 23):5'-CACGAGTGGAAAG-CAACTCA-3'
 OCT3/4-AS (SEQ ID NO: 24):5'-GCTTTCATGTC-CTGGGACTC-3'
(3) Mouse-GAPDH:
 GAPDH-S (SEQ ID NO: 25):5'-TGTCCGTCGTG-GATCTGAC-3'
 GAPDH-AS (SEQ ID NO: 26):5'-CCTGCTTCACCAC-CTTCTTG-3'

Results

Figure 5:
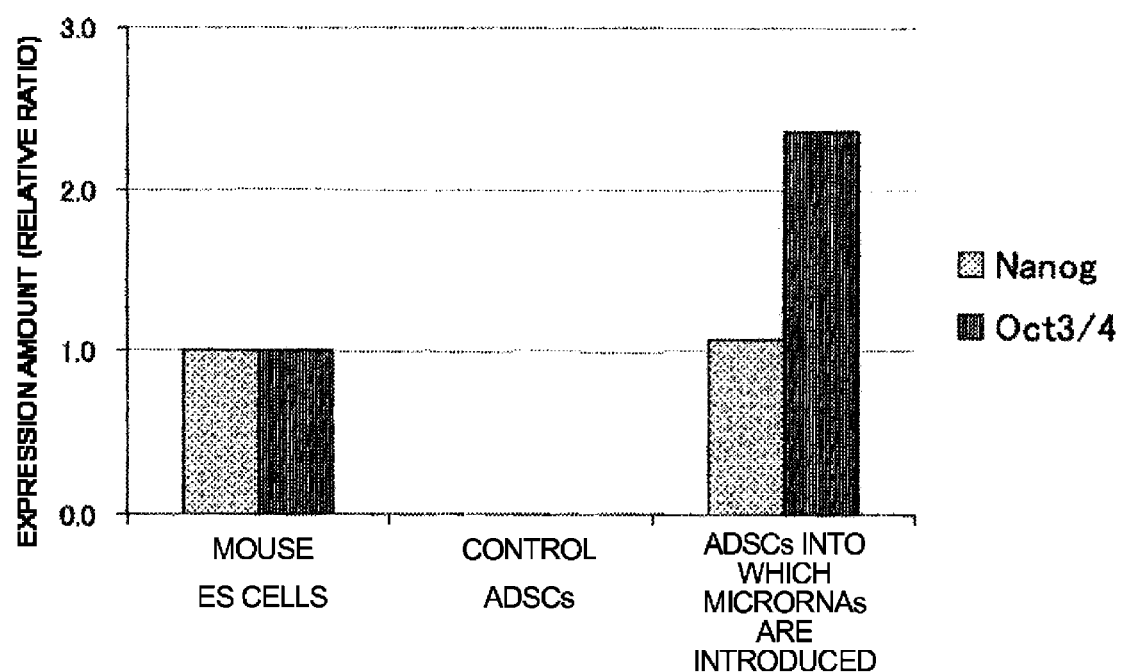
FIG. 5 shows a comparison between the expression amounts of mouse-NANOG and mouse-OCT3/4 in induced pluripotent stem cells produced using mouse adipose-derived stem cells (ADSCs) according to the method of the present invention and those in control mouse adipose-derived stem cells, in which microRNAs were not introduced (Example 5). The expression amounts of mouse-NANOG and mouse-OCT3/4 in the induced pluripotent stem cells were normalized using the expression amount of mouse-GADPH gene, and their relative ratio to those of mouse-NANOG and mouse-OCT3/4 in mouse ES cells are shown in the graph (n=3).

As shown in FIG. 5, expressions of mouse NANOG gene and mouse OCT3/4 gene were confirmed in the induced pluripotent stem cells of Example 3, as in ES cells. It was thus confirmed that the method of the present invention successfully produced cells having a property similar to that of ES cells.

Example 6

The induced pluripotent stem cells of Example 3 were evaluated in terms of rate of tumorigenesis.

Experiment Procedure

The induced pluripotent stem cells of Example 3 on Day 30 of microRNA introduction, a control cell group obtained by the same culture except for microRNA introduction, each in an amount of $1 \times 10^6$ cells, were diluted with a 100 μl D-MEM containing 10% FBS. Each solution was subcutaneously injected into the flank of a NOD/SCID mouse. The mice were raised for four weeks, and the tumorigenic potential was evaluated for each mouse.

Results

In contrast to Non-Patent Literature 3, in which tumorigenesis was observed four weeks after the subcutaneous injection, tumorigenesis was not observed in the mice injected with the induced pluripotent stem cells produced in Example 3 and the control cells (0 cases out of 6 cell groups with microRNA introduction; 0 cases out of 6 control cell groups).

Accordingly, it was found that the induced pluripotent stem cells produced by the method of the present invention has low possibility of tumorigenesis, compared with induced pluripotent stem cells produced with introduction of genes.

Example 7

An experiment was performed to produce induced pluripotent stem cells by reprogramming human dermal fibroblasts (HDF).

Experiment Procedure

Human dermal fibroblasts (HDF) (CA106K05a, Toyobo) were cultured in a D-MEM+10% FBS culture medium. In the same manner as in Examples 1 to 3, chemically synthesized microRNAs of hsa-miR-200c (SEQ ID NO: 13), hsa-miR-302a (SEQ ID NO: 14), hsa-miR-302b (SEQ ID NO: 15), hsa-miR-302c (SEQ ID NO: 16), hsa-miR-302d (SEQ ID NO: 17), hsa-miR-369-3p (SEQ ID NO: 18), hsa-miR-369-5p (SEQ ID NO: 19) and hsa-miR-369-3p (SEQ ID NO: 20) were transfected.

The transfected somatic cells were further cultured in the same manner as in Examples 1 to 3. On Day 20 of microRNA transfection, the cells were observed using an all-in-one-type fluorescence microscopy system (product of Keyence).

Results

Figure 6:
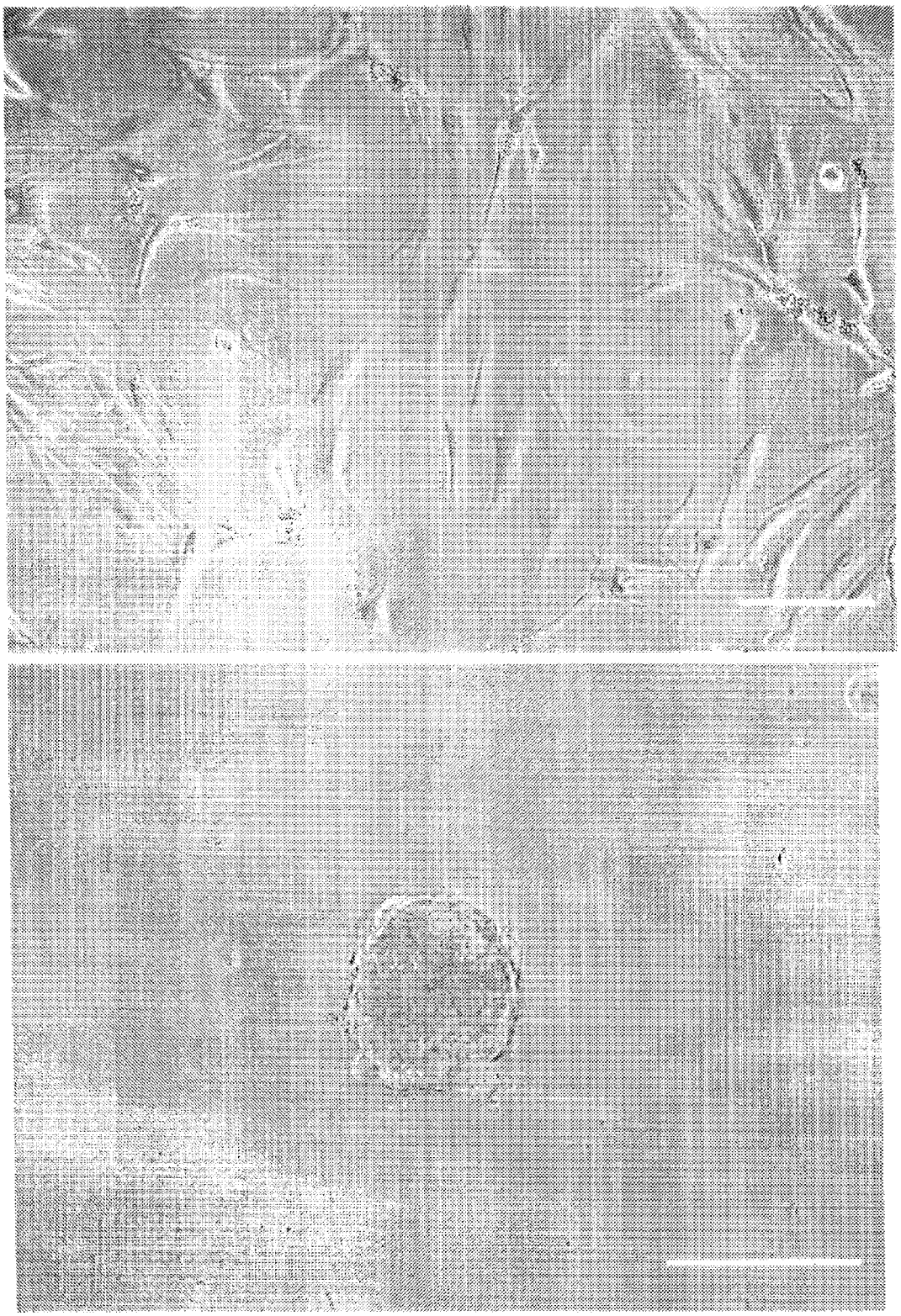
FIG. 6 shows a phase-contrast image of untreated human dermal fibroblasts (upper panel) and a phase-contrast image of induced pluripotent stem cells produced using human dermal fibroblasts according to the method of the present invention (lower panel) (Example 7). The scale bar indicates 100 μm.

As shown in FIG. 6, a spherical cell mass (embryoid body) was observed, which is a distinct form of a pluripotent stem cell. This form is clearly distinguished from the form of HDF cells as the control group (upper figure of FIG. 5). Accordingly, it was confirmed that the method of the present invention successfully produced induced pluripotent stem cells by reprogramming of human dermal fibroblasts.

The above results of Examples 1 to 7 showed that introduction of specific combinations of microRNAs into cells enables production of induced pluripotent stem cells with low possibility of tumorigenesis at a high induction efficiency. Further, the results of Examples 1 to 3 and Example 7 demonstrated production of induced pluripotent stem cells from various mammal-derived somatic cells.

Sequence Listing Free Text

SEQ ID NOs: 1 to 13 denote base sequences of mature microRNAs of mmu-miR-17, mmu-miR-21, mmu-miR-154, mmu-miR-200c, mmu-miR-294, mmu-miR-302a, mmu-miR-302b, mmu-miR-302c, mmu-miR-302d, mmu-miR-367, mmu-miR-369-3p, mmu-miR-369-5p and mmu-miR-370.

SEQ ID NOs: 14 to 20 denote base sequences of mature microRNAs of hsa-miR-200c, hsa-miR-302a, hsa-miR-302b, hsa-miR-302c, hsa-miR-302d, hsa-miR-369-3p and hsa-miR-369-5p.

SEQ ID NOs: 21 and 22 denote base sequences of primers to amplify mouse-NANOG gene.

SEQ ID NOs: 23 and 24 denote base sequences of primers to amplify mouse-OCT3/4 gene.

SEQ ID NOs: 25 and 26 denote base sequences of primers to amplify mouse-GADPH gene.

The invention claimed is:

1. A method for producing induced pluripotent stem cells comprising the step of introducing miR-200, miR-302 and miR-369 into isolated somatic cells and culturing said cells to produce induced pluripotent stem cells.

2. The method of claim 1, wherein at least one of the miR-200, miR-302, and miR-369 is a mature miRNA.

3. The method of claim 1, wherein the miR-200 is an at least one miRNA selected from the group consisting of has-miR-200a, has-miR-200b, has-miR-200c, mmu-miR-200a, and mmu-miR-200b.

4. The method of claim 1, wherein miR-302 is at least one miRNA selected from the group consisting of has-miR-302a, has-miR-302b, has-miR-302c, has-miR-302d, has-miR-302e, has-miR-302f, mmu-miR-302a, mmu-miR-302b, mmu-miR-302c, and mmu-miR-302d.

5. The method of claim 1, wherein miR-369 is at least one miRNA selected from the group consisting of has-miR-369-3p, has-miR-369-5p, mmu-miR-369-3p, and mmu-miR-369-5p.

6. The method of claim 1, wherein the miR-200, miR-302, and miR-369 are introduced into somatic cells in a way that none of the microRNAs are integrated into the genome DNA.

7. The method of claim 1, wherein the miR-200, miR-302, and miR-369 are introduced into somatic cells by lipofection.

8. The method of claim 1, wherein the miR-200, miR-302, and miR-369 are introduced into somatic cells in an amount sufficient to induce pluripotency of the cells.

* * * * *